United States Patent [19]

Duby et al.

[11] Patent Number: 5,446,171
[45] Date of Patent: Aug. 29, 1995

[54] PREPARATION OF 2-ACETYL-1-PYRROLINE

[75] Inventors: Philippe Duby, Prilly; Tuong Huynh-Ba, Pully, both of Switzerland

[73] Assignee: Nestec S.A., Vevey, Switzerland

[21] Appl. No.: 364,713

[22] Filed: Dec. 27, 1994

Related U.S. Application Data

[62] Division of Ser. No. 158,934, Nov. 29, 1993, Pat. No. 5,401,521, which is a division of Ser. No. 979,293, Nov. 20, 1992, Pat. No. 5,280,127.

Foreign Application Priority Data

Dec. 2, 1991 [CH] Switzerland ............... 03529/91

[51] Int. Cl.$^6$ ............................ C07D 207/20
[52] U.S. Cl. ..................... 548/540; 548/565
[58] Field of Search ............................ 558/540

[56] References Cited

U.S. PATENT DOCUMENTS

| | | | |
|---|---|---|---|
| 3,620,771 | 11/1971 | Hunter et al. | 260/297 R X |
| 3,725,425 | 4/1973 | Hunter et al. | 260/297 R |
| 4,522,838 | 6/1985 | Buttery et al. | 426/537 |
| 5,280,127 | 1/1994 | Duby et al. | 548/565 |

FOREIGN PATENT DOCUMENTS

| | | |
|---|---|---|
| 0436481 | 7/1991 | European Pat. Off. . |
| 1167809 | 10/1969 | United Kingdom . |

OTHER PUBLICATIONS

Abstract No. *84327 D/46* of Japanese Patent No. JS 6125-364 (1980).
Buchi, et al., "Synthesis of 2-Acetyl-1,4,5,6,-Tetrahydro-Pyridine, A Constituent of Bread Aroma," J. Org. Chem., vol. 36, No. 4, (1971) pp. 609–610.
Buttery, et al., "Cooked Rice Aroma and 2-Acetyl-1-Pyrroline," J. Agric. Food. Chem., (1983) 31, pp. 823–826.

*Primary Examiner*—Joseph Paul Brust
*Attorney, Agent, or Firm*—Vogt & O'Donnell

[57] ABSTRACT

2-acetyl-1-pyrroline is prepared by hydrolyzing a 2-(1-alkoxyethenyl)-1-pyrroline compound with an acid to obtain a reaction medium and then adding an equimolar amount of a base to the reaction medium to obtain a neutralized reaction medium containing 2-acetyl-1-pyrroline.

10 Claims, No Drawings

PREPARATION OF 2-ACETYL-1-PYRROLINE

CROSS REFERENCE TO RELATED APPLICATION

This application is a divisional application of application Ser. No. 08/158,934, filed Nov. 29, 1993, now U.S. Pat. No. 5,401,521, and which, in turn, is a divisional application of application Ser. No. 07/979,293, filed Nov. 20, 1992, now U.S. Pat. No. 5,280,127.

BACKGROUND OF THE INVENTION

This invention relates to a process for the production of 2-acetyl-1-pyrroline.

U.S. Pat. No. 4,522,838 (Buttery, et al.), describes a process for the production of 2-acetyl-1-pyrroline. This process comprises catalytically reducing 2-acetyl pyrrole for 15 hours under a hydrogen pressure of approximately 0.7 bar, to obtain (1-hydroxyethyl)-2-pyrrolidine as an intermediate product, and oxidizing the intermediate product obtained with silver carbonate under reflux in benzene, again over a period of 15 hours. The 2-acetyl-1-pyrroline is then isolated by gas phase chromatography using a capillary column 2 metres in length and 6.4 mm in diameter. The 2-acetyl-1-pyrroline thus obtained has a purity of approximately 95%, but can only be produced in small quantities at a time, due mainly to the purification of the compound by gas phase chromatography. In addition, the 2-acetyl-1-pyrroline is unstable and has to be stored at a temperature preferably below 0° C., which makes it difficult to use, particularly on an industrial scale.

Another process for the production of 2-acetyl-1-pyrroline from pyrroline is known from European Patent Application Publication No. 436 481, but does not solve the problem in question.

SUMMARY OF THE INVENTION

The present invention provides a process for preparing 2-acetyl-1-pyrroline by hydrolyzing a 2-(1-alkoxyethenyl)-1-pyrroline compound with an acid to obtain a reaction medium and then adding an equimolar amount of a base to the reaction medium to obtain a neutralized reaction medium containing 2-acetyl-1-pyrroline.

DETAILED DESCRIPTION OF THE INVENTION

In carrying out the present invention, a 2-(1-alkoxyethenyl)-1-pyrroline compound, which may be 2-(1-ethoxyethenyl)-1-pyrroline, is hydrolyzed with an acid, preferably a mineral acid, such as hydrochloric acid, and then, the reaction medium is neutralized with an equimolar amount of a base, preferably a strong base, such as sodium hydroxide, which may be added by dropwise addition with stirring. The 2-(1-alkoxyethenyl)-1-pyrroline compound to be hydrolyzed preferably is in a concentration of from 2% to 30%, and the reaction medium obtained by hydrolysis may be diluted with water before addition of the base.

Isolation of the 2-acetyl-1-pyrroline in a powder-form with a support provides a stable form which can be stored for a certain time at ambient temperature. In this case, a support substance of cyclodextrin, maltodextrin, or combinations thereof is combined with the reaction medium, which provides a support solution, and then, the support solution is freeze-dried.

When the support employed is cyclodextrin, it is combined in solution or in a dry form with the neutralized solution so that a solution containing up to 20% by weight 2-acetyl-1-pyrroline, based on the weight of the cyclodextrin, is obtained. β-cyclodextrin preferably is employed.

When the support is maltodextrin, it is combined in solution or in a dry form with the neutralized solution so that a solution containing up to 10% by weight 2-acetyl-1-pyrroline, based on the weight of the maltodextrin, is obtained. Additionally, gum arabic also may be incorporated into the neutralized solution with the maltodextrin.

The foregoing steps preferably are carried out at a temperature in the range of from −10° C. to 25° C., and it is important to bear in mind that the higher the temperature, the greater the risk of decomposition of the 2-acetyl-1-pyrroline and the greater the need to work quickly to reduce that risk.

After support addition, the support solution is freeze-dried, and when the support is added in dry form, rather than in solution, such may enable reduction of the amount of water to be removed, which thereby facilitates the freeze-drying.

Operating in accordance with the present invention, therefore, enables obtaining a composition of 2-acetyl-1-pyrroline incorporated with a support in a form of a powder which may contain up to 20% by weight of 2-acetyl-1-pyrroline based on the weight of the powder.

Accordingly, the present invention also relates to the use of 2-(1-alkoxyethenyl)-1-pyrroline compounds which corresponds to the following general formula:

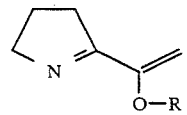

These compounds may be obtained by a process in which the corresponding alkyl vinylethyl compound is reacted with tert-butyl lithium in organic solution, for example in pentane, tetrahydrofuran or ether, or in a mixture of these solvents, N-trimethylsilyl-2-pyrrolidinone is then added and the mixture is left to react, preferably below 0° C., the solution obtained is hydrolyzed, the organic phase is recovered, dried and purified to obtain the required 2-(1-alkoxyethenyl)-1-pyrroline. The hydrolysis is preferably carried out by addition of water or a solution of ammonium chloride. After hydrolysis, a salt, such as sodium chloride, may be added to saturate the solution so that the yield of the process can be improved.

The final purification step may be carried out by any method, such as distillation and/or column chromatography.

Accordingly, compounds of the 2-(1-alkoxyethenyl)-1-pyrroline type can be obtained by this process and may be used for the production of 2-acetyl-1-pyrroline. It has also been found that one of the compounds of this type, namely 2-(1-ethoxyethenyl)-1-pyrroline, has certain organoleptic qualities which enable it to be used on its own or in combination as a flavouring agent. These organoleptic characteristics may be described as grilled, fruity, hazel nuts and reminiscent of those of pyrazine.

EXAMPLES

The invention is illustrated in more detail in the following Examples in which parts and percentages are by weight wherein Examples 1–3 illustrate preparation and properties of 2-(1-ethoxyethenyl)-1-pyrroline, and Examples 4–16 illustrate preparation of 2-acetyl-1-pyrroline and preparation of compositions including that compound incorporated with a support and properties thereof.

EXAMPLE 1

A solution containing 54.1 g ethylvinyl ether in 300 ml tetrahydrofuran (THF) is prepared.

This solution is cooled to −40° C. and a 1.4N solution of 429 ml tert-butyl lithium in pentane is added dropwise to the solution. The mixture is then stirred continuously for 12 hours at −40° C., after which a solution of 47.1 g of N-trimethylsilyl-2-pyrrolidinone in 300 ml THF is added. The mixture thus obtained is stirred continuously for 7 hours at −40° C., after which 32.1 g ammonium chloride dissolved in 300 ml water are added. The mixture is then left to return to approximately 0° C. and is then saturated by addition of 60 g sodium chloride. The solution is then left standing so that the aqueous phase and organic phase can separate. The organic phase is recovered and the aqueous phase is extracted three times with 50 ml ether.

The various organic fractions obtained are mixed, washed three times with 50 ml water saturated with NaCl and then dried over sodium sulfate and the solvents are evaporated under reduced pressure. 37.8 g crude extract are obtained in the form of a yellow liquid. A chromatography column 4 cm in diameter and 80 cm in height containing 500 g of a silica gel is prepared. A solution containing 20 parts dichloromethane to 1 part ethyl acetate is used as eluent. The crude extract diluted with the eluent is introduced into the column and is then eluted at a rate of 2 ml per minute. A 99.9% pure compound in the form of a colourless liquid is obtained in a yield of 17.1 g.

EXAMPLE 2

1. Mass Spectrum

The mass spectrum of the compound obtained in accordance with Example 1 gives the following results:

| m/z | Relative intensity (100 = base peak) | Identification |
|---|---|---|
| 139 | 8 | [M]+ Molecular peak |
| 124 | 21 | [M—CH$_3$]+ |
| 110 | 5 | [M—C$_2$H$_5$]+ |
| 95 | 100 | [M—CH$_3$CHO]+ |
| 94 | 66 | [M—OC$_2$H$_5$]+ |
| 83 | 6 | — |
| 82 | 10 | — |
| 67 | 18 | — |
| 41 | 30 | — |

2. Elemental Analysis

Elemental analysis of the compound obtained in accordance with Example 1 by combustion gave the following results:

| | | % |
|---|---|---|
| C | Observed | 68.70 |
| | Calculated | 69.03 |
| H | Observed | 9.26 |
| | Calculated | 9.41 |
| N | Observed | 9.74 |

| | % |
|---|---|
| Calculated | 10.06 |

The calculated results are for a compound having the approximate formula C$_8$H$_{13}$NO and a molecular weight M of 139.198 g.

3. Infrared Spectrum

The infrared spectrum of the compound obtained in accordance with Example 1 in the form of a film gives the following results:

| Frequency of the characteristic bands (cm$^{-1}$) | % Transmission |
|---|---|
| 2977 | 23.8 |
| 2932 | 28.9 |
| 2862 | 34.5 |
| 1738 | 45.8 |
| 1612 | 26.9 |
| 1591 | 20.5 |
| 1370 | 29.7 |
| 1322 | 19.7 |
| 1271 | 25.1 |
| 1129 | 20.6 |
| 1068 | 25.6 |
| 979 | 34.7 |
| 819 | 30.2 |

4. NMR Spectrum

The nuclear magnetic resonance spectrum of the proton of the compound in trichlorodeuteromethane (CDCl$_3$) at 20° C. shows the following characteristic signals:

| Signal (ppm) | Multiplicity of the signal | Coupling constant (Hz) | Identification |
|---|---|---|---|
| 4.73 | Doublet | 2.6 | H olefinic |
| 4.52 | Doublet | 2.6 | H Olefinic |
| 4.02 | Triplet of a triplet | 2.0 and 7.4 | 2H-5 |
| 3.87 | Quadruplet | 7 | 2H Ethyl |
| 2.73 | Multiplet | | 2H-3 |
| 1.93 | Multiplet | | 2H-4 |
| 1.42 | Triplet | 7 | 3H Ethyl |

Accordingly, the compound can be identified by these four tests as being 2-(1-ethoxyethenyl)-1-pyrroline corresponding to the following formula:

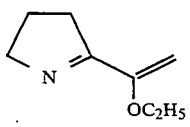

EXAMPLE 3 a) Detection of the Perception Threshold by Direct Olfaction

Several aqueous solutions containing 2-(1-ethoxyethenyl)-1-pyrroline in various concentrations are prepared.

50 ml of each solution accommodated in a 250 ml Erlenmeyer flask provided with a cover are presented to six tasters skilled in the analysis of aromas.

The test is carried out as follows:

Three flasks are presented to each taster: one flask containing the aromatic solution and two flasks containing water. The taster has to sniff the head space and designate the flask containing the aromatic solution. The test is repeated twice for concentrations of 1000, 100, 10, 5 and 1 ppm.

The following results are obtained:

| Concentration (ppm) | 1000 | 100 | 10 | 5 | 1 |
|---|---|---|---|---|---|
| Positive olfaction (%) | 100 | 100 | 100 | 50 | 17 |

Accordingly, the perception threshold by direct olfaction is of the order of 5 ppm. b)

Detection of the Perception Threshold by GC Sniffing

The minimum quantity of 2-(1-ethoxyethenyl)-1-pyrroline detectable by olfaction is determined by GC sniffing (a combination of gas chromatography and olfactometry). To this end, solutions of the compound in various concentrations are analyzed by gas phase chromatography.

After orientation tests, solutions of 2-(1-ethoxyethenyl)-1-pyrroline in dichloromethane are prepared in concentrations of 100, 500 and 1000 ppm.

The analyses are carried out under the following conditions:

| | |
|---|---|
| Chromatograph | HP 5890 A (Hewlett Packard) |
| Capillary column | DB wax (J and W Scientific), length 30 m, i.d. 0.25 mm |
| Detection | FID, 250° C. + sniffing port, 150° C. effluent splitting: 1/1 |
| Injection | 200° C., split (27.7 ml/min.) |
| Gas vector | helium, 17.5 psi |
| Furnace temperature: | 100° C. - 4° C./min. - 180° C. |
| Quantity injected: | 1 microlitre of a 1000 ppm solution, i. e., 1 microgram of the compound. |
| Gas flows: | split vent = 27.7 ml/min. column effluent = 0.6 ml/min. (sniffing port) |
| Quantity of 2-(1-ethoxyethenyl)-1-pyrroline arriving at the sniffing port = 21.7 ng | |
| Estimation of the air volume entraining the 2-(1 ethoxyethenyl)-1-pyrroline | |
| Duration of olfactory peak = 5 seconds | |
| Humidified air flow rate (make up) = 0.83 ml/sec. | |
| Air volume estimated at 4.2 ml air. | |

The perception threshold of 2-(1-ethoxyethenyl)-1-pyrroline is 21.7 ng in 4.2 ml air, i.e., 5.20 ng/ml air.

EXAMPLE 4

2-(1-Ethoxyethenyl)-1-pyrroline is hydrolzed by addition of 5 ml 10.5N hydrochloric acid to 67.74 mg 2-(1-ethoxyethenyl)-1-pyrroline at 0° C. The mixture is then left standing for 2 hours at ambient temperature (25° C.).

The mixture is then cooled to approximately 5° C. and neutralized by dropwise addition with continuous stirring of 52.5 ml 1N sodium hydroxide. An aqueous solution containing 97% 2-acetyl-1-pyrroline, i.e., 52.40 mg, and 3% 2-acetyl-2-pyrroline, i.e., 1.62 mg (composition determined by gas phase chromatography and mass spectrometry) is obtained.

EXAMPLE 5

2-(1-Ethoxyethenyl)-1-pyrroline is hydrolyzed by addition of 5 ml 1N hydrochloric acid to 69.81 mg 2-(1-ethoxyethenyl)-1-pyrroline at 0° C. The mixture is then left standing for 7 days at ambient temperature (25° C.) so that hydrolysis is complete.

The mixture is then cooled to approximately −5° C. and the hydrolyzed mixture is diluted with 40 ml water and then neutralized by dropwise addition with continuous stirring of 5 ml 1N sodium hydroxide.

An aqueous solution containing 54 mg 2-acetyl-1-pyrroline (97%) and 1.67 mg 2-acetyl-2-pyrroline (3%) is obtained.

EXAMPLE 6

70 ml 1N HCl are added to 1.00132 g 2-(1-ethoxyethenyl)-1-pyrroline (i.e., 7.20 mmol) at 0° C. and the mixture is left standing for 7 days at ambient temperature.

A first sample A of 17.5 ml of this reaction mixture is diluted in 175 ml water and cooled to 0° C. 17.5 ml 1N NaOH and an aqueous solution containing 17.6 g maltodextrin, 2.4 g gum arabic and 430 ml water are then added dropwise. The solution thus obtained is freeze-dried in a standard freeze dryer. A white powder containing 2-acetyl-1-pyrroline in a concentration of 1.0%, based on the maltodextrin/gum arabic mixture, and in a concentration of 0.94%, based on the powder, is obtained.

EXAMPLE 7

A sample B of 13.125 ml of the reaction mixture obtained in Example 6 is diluted in 130 ml water and cooled to 0° C. 13.125 ml 1N NaOH and then an aqueous solution containing 15 g β-cyclodextrin in 400 ml water are then added dropwise. The solution thus obtained is freeze-dried as in Example 6. A white powder containing 2-acetyl-1-pyrroline in a concentration of 1.0%, based on the β-cyclodextrin, and in a concentration of 0.94%, based on the powder, is thus obtained.

EXAMPLE 8

A sample C of 13.125 ml of the reaction mixture obtained in Example 6 is diluted in 100 ml water and then cooled to 0° C. 15.0 g β-cyclodextrin in powder form and 13.125 ml 1N NaOH are then added. After stirring for 30 minutes at 0° C., the solution is freeze-dried as in Example 6. In this case, freeze-drying is easier to carry out because the volume of water is much smaller by comparison with Examples 6 and 7.

A white powder containing 2-acetyl-1-pyrroline in a concentration of 1.0%, based on the β-cyclodextrin, and 0.94%, based on the powder, is obtained.

EXAMPLE 9

A sample D of 13.125 ml of the reaction mixture obtained in Example 6 is diluted in 130 ml water and cooled to 0° C. 13.125 ml 1N NaOH and an aqueous solution containing 1.5 g β-cyclodextrin in 40 ml water are then added dropwise. The solution thus obtained is freeze-dried as in Example 6. A white powder containing 2-acetyl-1-pyrroline in a concentration of 10.0%, based on the β-cyclodextrin, is obtained.

EXAMPLE 10

The stability of the 2-acetyl-1-pyrroline prepared in accordance with Examples 6 to 9 is studied over a period of 110 days at various storage temperatures. To this end, samples of 100 mg freeze-dried powder are taken after storage and dissolved in 1 ml water at 0° C. 1 ml ethyl acetate containing 1 mg trimethyl-2,4,6-pyridine is added and the mixture is stirred for 30 seconds. The mixture is then centrifuged for 15 minutes at −5° C. and the organic phase is recovered and analyzed by gas phase chromatography.

The percentage of 2-acetyl-1-pyrroline being decomposed after 110 days storage is then determined. The following results are obtained:

| | Support and % decomposition of 2-acetyl-1-pyrroline | | |
|---|---|---|---|
| Storage temperature | Maltodextrin 1% | β-Cyclodextrin 1% | β-Cyclodextrin 10% |
| 20° C. | Complete decomposition after 50 d | 99% | 91% After 13 days |
| 4° C. | 33% | 10% | 13% After 23 days |
| −20° C. | 13% | 0% | — |

It can be seen that 2-acetyl-1-pyrroline in a concentration of 1% on β-cyclodextrin remains stable for at least 110 days when stored at a low temperature. This is also the case, although to a lesser extent, if the 2-acetyl-1-pyrroline is in a concentration of 1% on maltodextrin/gum arabic. By contrast, the stability of the 2-acetyl-1-pyrroline decreases when its concentration on the support (in the present case β-cyclodextrin) increases. By comparison, 95% pure 2-acetyl-1pyrroline prepared in accordance with the prior art degrades rapidly in storage at −20° C. (Buttery, et al., Journal of Agric. Food Chem. (1983), 31, 823–826).

EXAMPLE 11

1 ppm 2-acetyl-1-pyrroline in a concentration of 1% on β-cyclodextrin is added to a corn soup just before consumption. The soup thus prepared and a control soup containing no 2-acetyl-1-pyrroline are presented to a group of six trained tasters. The 2-acetyl-1-pyrroline contributes towards a rounder, more cooked and more pleasant perception of the food. The "cooked cereal", "popcorn" and "very slightly grilled" notes are strengthened and developed together with a very fine "buttery-fresh" note.

EXAMPLE 12

1 ppm 2-acetyl-1-pyrroline in a concentration of 1% on β-cyclodextrin is added to a chicken soup just before its consumption. The soup thus prepared and a control soup containing no 2-acetyl-1-pyrroline are presented to a group of six trained tasters. The 2-acetyl-1-pyrroline contributes towards reducing the "chicken fat" note and strengthens the "chicken meat" and "slightly grilled" notes. The whole is more cooked and more complete and the slight "grilled meat" aftertaste is prolonged.

EXAMPLE 13

1 ppm 2-acetyl-1-pyrroline in a concentration of 1% on β-cyclodextrin is added to a beef soup just before consumption. The soup thus prepared and a control soup containing no 2-acetyl-1-pyrroline is presented to a group of six trained tasters. The 2-acetyl-1-pyrroline contributes towards strengthening the "slightly grilled meat" note. The impression in the mouth is more round and the beef aftertaste is prolonged.

EXAMPLE 14

A composition of the "breadcrust" type is prepared by adding the following compounds to 1 liter ethanol: 50 g 2-acetyl pyrazine, 10 g 2-acetyl thiazole, 30 g diacetyl, 5 g 2-ethyl-3-methyl pyrazine. 0.1 g of this composition is added to 1 liter water previously salted with 3 g NaCl per liter. The aqueous mixture is divided into two batches. 0.5 ppm 2-acetyl-1-pyrroline in a concentration of 1% on β-cyclodextrin is added to the first batch. The second batch serves as control. A panel of ten people compares the two batches. The first batch appears better than the second with a strengthened "cereal", "breadcrust" note and a rounded "grilled" note. The whole remains longer in the mouth. When added to a pizza dough, the present composition strengthens the "breadcrust" note, above all on olfaction.

EXAMPLE 15

A composition of the "corn" type is prepared by adding the following compounds to 1 liter ethanol: 5 g 2-acetyl pyrazine, 5 g 2-acetyl thiazole, 0.5 g diacetyl, 20 g dimethyl sulfide. 0.1 g of this composition is added to 1 liter water salted beforehand with 3 g NaCl per liter the aqueous mixture is divided into two batches. 0.5 ppm 2-acetyl-1-pyrroline in a concentration of 1% on β-cyclodextrin is added to the first batch. The second batch serves as control. A panel of 10 people compares the two batches. The first batch has a more marked, more complete and more powerful "sweet corn" and "popcorn" note. Persistence in the mouth is more pronounced.

EXAMPLE 16

A composition of the "potato" type is prepared by adding the following compounds to 1 liter ethanol: 5 g 2-acetyl thiazole, 5 g trimethyl pyrazine, 0.5 g diacetyl, 2 g 2-ethyl-3-methoxypyrazine, 50 g methylthio-3-propanal. 0.1 g of this composition is added to 1 liter water salted beforehand with 3 g NaCl per liter. The aqueous mixture is divided into two batches. 0.5 ppm 2-acetyl-1-pyrroline in a concentration of 1% on β-cyclodextrin is added to the first batch. The second batch serves as control. A panel of 10 people compares the two batches. The first batch appears better than the second and has a more complete and strengthened note of the "cooked potato flesh" type.

We claim:

1. A process for preparing 2-acetyl-1-pyrroline comprising hydrolyzing a 2-(1-alkoxyethenyl)-1-pyrroline compound with an acid to obtain a reaction medium and then adding an equimolar amount of a base to the reaction medium to obtain a neutralized reaction medium containing 2-acetyl-1-pyrroline.

2. A process according to claim 1 wherein the 2-(1-alkoxyethenyl)-1-pyrroline compound is 2-(1-ethoxyethenyl)-1-pyrroline.

3. A process according to claim 1 or 2 wherein the process is carried out at a temperature of from −10° C. to 25° C.

4. A process according to claim 1 or 2 wherein the base is added dropwise to the reaction medium.

5. A process according to claim 1 or 2 further comprising diluting the reaction medium with water prior to adding the base.

6. A process according to claim 1 or 2 wherein the acid and 2-(1-alkoxyethenyl)-1-pyrroline are added together for hydrolysis so that the 2-(1-alkoxyethenyl)-1-pyrroline is in a concentration of from 2% to 30% by weight.

7. A process according to claim 1 or 2 wherein the acid is a mineral acid and wherein the base is a strong base.

8. A process according to claim 1 or 2 wherein the acid is hydrochloric acid.

9. A process according to claim 1 or 2 wherein the base is sodium hydroxide.

10. A process according to claim 1 or 2 wherein the acid is hydrochloric acid and wherein the base is sodium hydroxide.

* * * * *

UNITED STATES PATENT AND TRADEMARK OFFICE
CERTIFICATE OF CORRECTION

PATENT NO. : 5,446,171
DATED : August 29, 1995
INVENTOR(S) : Duby, et al.

It is certified that error appears in the above-indentified patent and that said Letters Patent is hereby corrected as shown below:

Title page, first line under the heading OTHER PUBLICATIONS, change "JS 6125-364" to --J5 6125-364--.

Column 2, line 37, after "O-R", insert --with R = alkyl.--.

Signed and Sealed this

Thirty-first Day of October 1995

Attest:

BRUCE LEHMAN

Attesting Officer     Commissioner of Patents and Trademarks